(12) United States Patent
Madaus et al.

(10) Patent No.: US 9,789,274 B2
(45) Date of Patent: *Oct. 17, 2017

(54) RESPIRATORY MASK ARRANGEMENT AS WELL AS HEADBAND ARRANGEMENT AND RESPIRATORY GAS EVACUATION DEVICE FOR A RESPIRATORY MASK

(75) Inventors: Stefan R. Madaus, Krailling (DE); Caspar Graff Stauffenberg, Gauting (DE); Harald Vogele, Gauting (DE)

(73) Assignee: ResMed R&D Germany GmbH, Martinsried (DE)

( * ) Notice: Subject to any disclaimer, the term of this patent is extended or adjusted under 35 U.S.C. 154(b) by 1683 days.

This patent is subject to a terminal disclaimer.

(21) Appl. No.: 10/563,857

(22) PCT Filed: Jul. 9, 2004

(86) PCT No.: PCT/EP2004/007599
§ 371 (c)(1),
(2), (4) Date: Jul. 10, 2006

(87) PCT Pub. No.: WO2005/004963
PCT Pub. Date: Jan. 20, 2005

(65) Prior Publication Data
US 2007/0131229 A1 Jun. 14, 2007

(30) Foreign Application Priority Data

Jul. 9, 2003 (DE) .................................. 103 31 134
Jul. 30, 2003 (DE) .................................. 103 35 162

(51) Int. Cl.
*A61M 16/00* (2006.01)
*A61M 16/06* (2006.01)
*A61M 16/20* (2006.01)

(52) U.S. Cl.
CPC .......... *A61M 16/208* (2013.01); *A61M 16/06* (2013.01); *A61M 16/0616* (2014.02);
(Continued)

(58) Field of Classification Search
CPC ................ A61M 16/06; A61M 16/208; A61M 16/0616; A61M 16/0683; A61M 2205/42; A61M 2205/7536; A61M 2210/0618
(Continued)

(56) References Cited

U.S. PATENT DOCUMENTS 1,878,464 A * 9/1932 Bulmer ..................... 128/205.25
2,578,007 A * 12/1951 Hill .......................... 128/206.17
(Continued)

FOREIGN PATENT DOCUMENTS

| AU | 712236 | 4/1999 |
| DE | 693 28 158 | 10/2000 |

(Continued)

OTHER PUBLICATIONS

Notice of Reasons for Rejection and English Translation for copending Japanese Application No. 2012-009839, mailed Feb. 5, 2013, 6 pages.
(Continued)

*Primary Examiner* — Justine Yu
*Assistant Examiner* — Douglas Sul
(74) *Attorney, Agent, or Firm* — Nixon & Vanderhye P.C.

(57) ABSTRACT

The invention relates to a respiratory mask arrangement that can be used in the framework of CPAP therapy for treating sleep-related disturbances, for example. In one embodiment a respiratory mask arrangement comprises a sealing lip device to be placed on the facial surface of a mask user, a covering device which defines a mask interior in cooperation with the sealing lip device, and a respiratory gas conduit unit for delivering respiratory gas to the mask interior that is
(Continued)

defined by the covering device and is connected to the nostril and/or oral opening of the mask user. At least some sections of the covering device are embodied as an air-permeable structure.

39 Claims, 3 Drawing Sheets

(52) U.S. Cl.
CPC ..... *A61M 16/0683* (2013.01); *A61M 2205/42* (2013.01); *A61M 2205/7536* (2013.01); *A61M 2206/14* (2013.01); *A61M 2210/0618* (2013.01)

(58) Field of Classification Search
USPC ............ 128/204.18, 205.24–205.25, 206.12, 128/206.15, 206.21–206.29, 128/207.11–207.13, 206.18, 206.19
See application file for complete search history.

(56) References Cited

U.S. PATENT DOCUMENTS

| | | | |
|---|---|---|---|
| 2,931,356 A * | 4/1960 | Schwarz | 128/206.24 |
| 3,291,127 A | 12/1966 | Eimer et al. | |
| 3,850,171 A | 11/1974 | Ball et al. | |
| 3,865,106 A | 2/1975 | Palush | |
| 3,971,369 A * | 7/1976 | Aspelin et al. | 128/206.19 |
| 4,062,359 A | 12/1977 | Geaghan | |
| 4,258,710 A | 3/1981 | Reber | |
| 4,266,540 A | 5/1981 | Panzik et al. | |
| 4,422,456 A | 12/1983 | Tiep | |
| 4,600,002 A * | 7/1986 | Maryyanek et al. | 128/206.19 |
| 4,774,946 A | 10/1988 | Ackerman | |
| 4,820,289 A | 4/1989 | Coury et al. | |
| 4,944,310 A | 7/1990 | Sullivan | |
| 4,974,586 A | 12/1990 | Wandel et al. | |
| 5,065,756 A | 11/1991 | Rapoport | |
| 5,117,819 A | 6/1992 | Servidio et al. | |
| 5,148,802 A | 9/1992 | Sanders et al. | |
| 5,269,296 A | 12/1993 | Landis | |
| 5,465,712 A | 11/1995 | Malis et al. | |
| 5,477,852 A | 12/1995 | Landis et al. | |
| 5,538,000 A | 7/1996 | Rudolph | |
| 5,560,354 A | 10/1996 | Berthon-Jones et al. | |
| 5,644,807 A | 7/1997 | Battistella | |
| 5,647,358 A | 7/1997 | Vilasi | |
| 5,657,752 A | 8/1997 | Landis et al. | |
| 5,701,892 A * | 12/1997 | Bledstein | 128/206.19 |
| 5,765,557 A | 6/1998 | Warters | |
| 5,937,851 A | 8/1999 | Serowski et al. | |
| 5,989,235 A | 11/1999 | Quacquarella et al. | |
| 6,112,746 A | 9/2000 | Kwok et al. | |
| 6,119,693 A | 9/2000 | Kwok et al. | |
| 6,192,886 B1 | 2/2001 | Rudolph | |
| 6,357,440 B1 * | 3/2002 | Hansen et al. | 128/206.19 |
| 6,561,190 B1 | 5/2003 | Kwok | |
| 6,561,191 B1 | 5/2003 | Kwok | |
| 6,581,594 B1 * | 6/2003 | Drew et al. | 128/204.18 |
| 6,584,976 B2 | 7/2003 | Japuntich et al. | |
| 6,615,832 B1 * | 9/2003 | Chen | 128/206.26 |
| 6,662,803 B2 | 12/2003 | Gradon et al. | |
| 6,823,865 B2 | 11/2004 | Drew et al. | |
| 6,863,069 B2 | 3/2005 | Wood | |
| 6,948,499 B2 * | 9/2005 | Griesbach et al. | 128/206.25 |
| 7,080,645 B2 | 7/2006 | Genger et al. | |
| 7,086,422 B2 | 8/2006 | Huber et al. | |
| 7,178,526 B2 | 2/2007 | McDonald et al. | |
| 7,207,335 B2 | 4/2007 | Kwok et al. | |
| 7,318,437 B2 | 1/2008 | Gunaratnam et al. | |
| 7,637,288 B2 | 12/2009 | Huber et al. | |
| 2001/0032648 A1 | 10/2001 | Jestrabek-Hart | |
| 2002/0055685 A1 | 5/2002 | Levitsky et al. | |
| 2002/0092527 A1 | 7/2002 | Wood | |
| 2003/0075180 A1 | 4/2003 | Raje et al. | |
| 2003/0079751 A1 | 5/2003 | Kwok et al. | |
| 2003/0164170 A1 | 9/2003 | Drew et al. | |
| 2004/0016432 A1 | 1/2004 | Genger et al. | |
| 2004/0060562 A1 | 1/2004 | McDonald et al. | |
| 2004/0025885 A1 | 2/2004 | Payne | |
| 2005/0092326 A1 | 5/2005 | Drew et al. | |
| 2006/0260614 A1 | 11/2006 | Biener et al. | |
| 2007/0068526 A1 | 3/2007 | Lang et al. | |
| 2007/0101998 A1 | 5/2007 | Kwok et al. | |
| 2007/0175479 A1 | 8/2007 | Groll | |
| 2008/0142015 A1 | 6/2008 | Groll | |

FOREIGN PATENT DOCUMENTS

| | | |
|---|---|---|
| DE | 100 51 891 | 5/2002 |
| DE | 101 05 383 | 8/2002 |
| EP | 0 267 428 | 5/1988 |
| EP | 0 601 708 | 6/1994 |
| EP | 0 697 225 A2 | 2/1996 |
| EP | 1 027 905 A | 8/2000 |
| EP | 1 147 782 | 10/2001 |
| EP | 1 149 603 A2 | 10/2001 |
| EP | 1 314 445 A | 5/2003 |
| EP | 1 396 277 A2 | 10/2004 |
| JP | 2000-507887 | 6/2000 |
| WO | WO 97/34507 | 9/1997 |
| WO | 98/24499 A1 | 6/1998 |
| WO | 00/76568 A1 | 12/2000 |
| WO | WO 00/78381 A1 | 12/2000 |
| WO | WO 01/32250 A | 5/2001 |
| WO | WO 2001/062326 | 8/2001 |
| WO | WO 02/32491 A2 | 4/2002 |
| WO | 2009/105528 | 8/2009 |

OTHER PUBLICATIONS

Office Action issued in related CN Appln. No. 200580011118.3 (Feb. 22, 2012).
First Examination Report issued in a related Indian Patent Application No. 6006/delnp/2006 on Feb. 2, 2013.
Decision of Rejection and English Translation for Japanese Application No. 2011-047484, mailed Jul. 2, 2013 (4 pages).
International Preliminary Report on Patentability, International Application No. PCT/AU2005/000539, (Oct. 19, 2006), 6 pgs.
International Search Report for PCT/AU2005/000539 dated Jun. 21, 2005.
Supplementary Search Report issued in EP 05 72 9680 on Sep. 18, 2009.
Office Action issued in CN 200580011118.3 on Nov. 27, 2009.
Examination Report issued in NZ 550423 on Mar. 13, 2009.
Further Examination Report for copending NZ Application No. 595133, dated Dec. 18, 2012, 2 pages.
Office Action for copending U.S. Appl. No. 11/578,293, dated Jan. 4, 2013, 25 pages.
European Search Report for Corresponding European Appln. No. 10 18 0729, mailed Dec. 9, 2010, 10 pages.
Examination Report for corresponding NZ Appln No. 583929, Mailed Sep. 20, 2011, 2 pages.
Decision of Rejection and English Translation for corresponding JP Appln. No. 2007-507626, Mailed Sep. 20, 2011, 4 pages.
Notice of Reasons for Rejection and English Translation for Japanese Application No. 2011-047484, mailed Aug. 7, 2012 (6 pages).
U.S. Appl. No. 60/640,184, filed Dec. 2004, Henry et al.
Instruction Brochure for "E-vent-N" Aug. 1997, © Dräger Medizintechnik GmbH, 2 pages.
European Search Report for PCT/EP2004/007599, mailed Dec. 17, 2004, 10 pages.
Non-Final Office Action issued in related U.S. Appl. No. 11/578,293 including PTO-892 citing McDonald et al. (US 2004/0060562 A1), Dye (U.S. Pat. No. 5,795,312) and Norvell et al. (US 2001/0008672 A2).
Decision of Rejection issued in related Japanese Patent Application No. 2012-009839 on Dec. 24, 2013 with English-language translation.

(56) References Cited

OTHER PUBLICATIONS

Official Communication issued Jul. 17, 2015, in a corresponding European Patent Application No. EP 10 18 0729.5 (9 pages), and English translation thereof (8 pages).
Examiner's Answer issued Jul. 14, 2016 in a related U.S. Appl. No. 11/578,293 (17 pages), citing U.S. Patent Publication No. 2004/0060562 and U.S. Pat. No. 5,795,312.
Office Action dated Mar. 18, 2015 issued in related U.S. Appl. No. 11/578,293 citing U.S. Pat. No. 5,795,312 and US 2004/0060562 (13 pages).
Final Office Action issued Aug. 5, 2014 in related U.S. Appl. No. 11/578,293.
Appeal Decision issued Jul. 7, 2014 in related Japanese Application No. 2011-47484 with English translation thereof.
Final Office Action issued Aug. 28, 2015 in a related U.S. Appl. No. 11,578,293 (15 pages).
An Extended European Search Report dated Apr. 26, 2017, in a corresponding European Application No. EP 16 19 4458.2 (12 pages), and an English translation thereof (6 pages).
An Office Action dated Jul. 12, 2017, in a related U.S. Appl. No. 15/607,224 (24 pages).

\* cited by examiner

RESPIRATORY MASK ARRANGEMENT AS WELL AS HEADBAND ARRANGEMENT AND RESPIRATORY GAS EVACUATION DEVICE FOR A RESPIRATORY MASK

CROSS REFERENCE TO PRIORITY APPLICATION

This application is a national phase application of PCT/EP2004/007599, filed Jul. 9, 2004, which claims the benefit of German Application No. 103 31 134.3, filed Jul. 9, 2003 and German Application No. 103 35 162.0, filed Jul. 30, 2003, pending, each incorporated herein by reference in its entirety.

FIELD OF THE INVENTION

The invention relates to a respiratory mask arrangement, of the kind that can be used for instance in CPAP therapy for the treatment of sleep-related breathing disorders. The invention also relates to a headband arrangement for a respiratory mask and to a respiratory gas evacuation device for a respiratory mask arrangement, for evacuating CO2-laden respiratory mask.

BACKGROUND OF THE INVENTION

In the aforementioned CPAP therapy, a breathable gas, in particular ambient air, can be delivered to a patient via a respiratory mask at a pressure level that is above the ambient pressure level. By means of the respiratory gas that is under pressure, a pneumatic tracking of the upper airways can be attained, and any obstructions can thereby be averted. In carrying out a pressurized breathing or CPAP therapy, the respiratory mask arrangements required for delivering the respiratory gas are typically worn by the patient for the entire duration of the patient's sleeping or resting phase. The respiratory mask arrangement is typically braced via a sealing lip zone in the region surrounding the mask user's nose and via a forehead-mounted device in the region of the make user's forehead. The retention forces required to apply the respiratory mask arrangement may be brought to bear by a fixation device, which for example has a headband that extends around the back of the mask user's head. The evacuation of the respiratory gas, which may be laden with CO2, from the interior region of the respiratory mask can be done via bores whose open cross section is defined such that a sufficiently great outflow of the respiratory gas is made possible.

OBJECT OF THE INVENTION

It is the object of the invention to furnish embodiments by which a reliable evacuation of CO2-laden respiratory gas from the interior region of a respiratory mask arrangement is advantageously assured.

Attainment of the Object According to the Invention

In a first aspect, A respiratory mask arrangement having a sealing lip device for resting on the facial surface of a mask user, a covering device which in cooperation with the sealing lip device defines a mask interior, a respiratory gas evacuation device for delivering respiratory gas to the mask interior defined by the covering device, this mask interior communicating with the nostril and/or the oral opening of the mask user; the covering device is embodied at least in some portions as a permeable structure.

It thus becomes advantageously possible to create a respiratory mask arrangement which furnishes a gas outflow area that enables a diffuse outflow of gas while emitting little noise.

The covering device is preferably made from an air-permeable material, in particular GOR-TEX® material. As an alternative to this provision, or in combination with it, it is also possible to make the covering device from a porous material.

Especially advantageously, the covering device is made from a flexible material which is deployed or inflated in the mask interior under the influence of pressure. The air permeability of the air-permeable material and the area of the portion defined thereby are selected such that a sufficient outflow of gas from the mask interior is assured.

The covering device or the sealing lip device may be coupled with a headband arrangement. The headband arrangement itself may likewise be used to furnish a gas outflow area. This gas outflow area can be formed by a hoselike zone of an air-permeable hose material.

The sealing lip device is preferably glued or vulcanized or sprayed onto the covering device. It is also possible to couple the covering device detachably with the sealing lip device, or to embody the sealing lip device integrally with the covering device. It is possible to deploy the covering device by means of supporting wall structures.

The covering device may also have a hard shell body and a woven outlet portion coupled to the hard shell body. This woven outlet portion preferably has an area of at least 3.7 $cm^2$.

The invention also relates to a headband arrangement for a respiratory mask; the headband arrangement in at least some portions is made of an air-permeable material and includes a conduit unit which is in communication with a mask interior defined by the respiratory mask, in such a manner that an outflow from the mask interior of respiratory gas that is under pressure can be effected through the air-permeable material portion provided in the headband.

Advantageous features of this invention are the subject of the dependent claims.

The object stated initially above is also attained, in a further aspect, by a respiratory mask arrangement having an arched member, a sealing lip device for resting on the facial surface of a mask user, and a respiratory gas conduit unit for delivering respiratory gas to a mask interior that is defined by the arched member and is in communication with the nostril and/or the oral opening of the mask user; in cooperation with the arched member, an air guide path is defined that extends from a respiratory gas inlet area to a respiratory gas outlet area and extends at least in some portions along a wall defining the arched member.

As a result, it advantageously becomes possible to create a respiratory mask arrangement that is easily cleaned and is distinguished by low noise and an only slight idle volume.

BRIEF DESCRIPTION OF THE DRAWINGS

Further details and characteristics of the invention will become apparent from the ensuing description in conjunction with the drawings. Shown are:

FIG. 8b, a sketch for explaining a preferred internal design of a hard shell with a receiving portion for receiving the insert element of FIG. 8a.

DETAILED DESCRIPTION OF THE DRAWINGS

Figures 1, 2, 3, 4, 5:
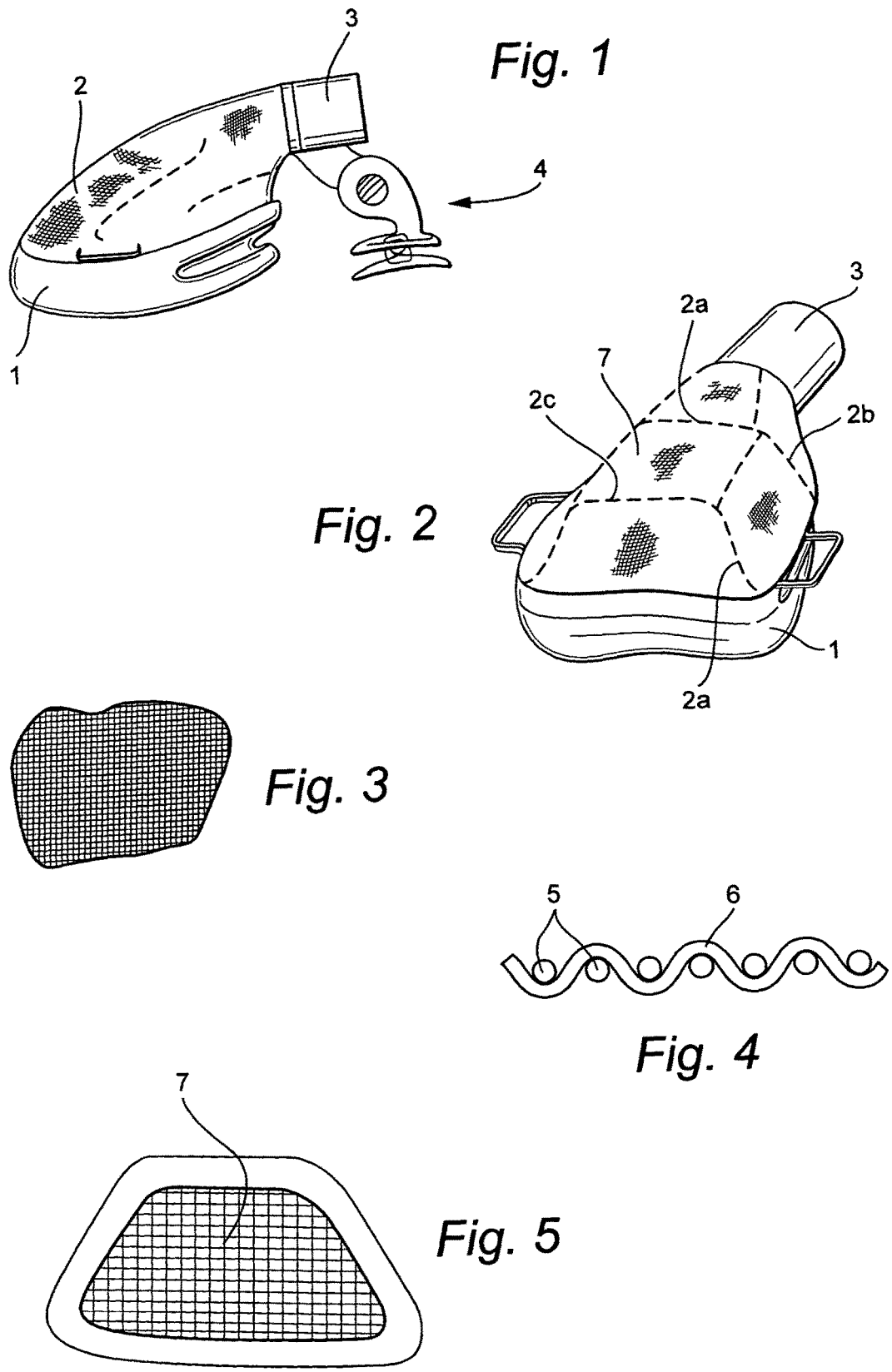
FIG. 1, a sketch for explaining a first embodiment of a respiratory mask according to the invention.
FIG. 2, a sketch for explaining a second embodiment of a respiratory mask.
FIG. 3, a sketch for explaining a woven material portion.
FIG. 4, a sketch for explaining the micropore structure obtained by a loose hook-and-loop fastening in a woven material.
FIG. 5, a sketch for explaining an outlet insert, formed of a woven material, for a hard shell for the mask.

The respiratory mask arrangement shown in FIG. 1 includes a sealing lip device 1, made from an elastomer material, in particular silicone rubber, and a covering device 2. The sealing lip device 1 is embodied such that it encompasses a receiving opening, intended to receive the nasal region of a mask user, and preferably crosses over the bridge of the nose and the upper lip region of the mask user. The sealing lip device 1 thus has a substantially saddle-shaped silhouette.

The covering device 2 is embodied such that in cooperation with the sealing lip device 1, it defines a mask interior. The mask interior is in communication with a respiratory gas conduit unit 3, for delivering respiratory gas to the mask interior defined by the covering device and communicating with the nostril and/or the oral opening of the mask user. The covering device is embodied in at least some portions as an air-permeable woven structure. The respiratory gas conduit unit 3 forms a connection stub for coupling a respiratory gas hose. The respiratory mask arrangement shown serves to deliver respiratory gas at a pressure level that is above the ambient pressure. Under the influence of the pressure, the covering device 2 is deployed in the mask interior between its peripheral attachment points, that is, between the sealing lip device 2 and the respiratory gas conduit unit 3.

FIG. 2 shows a further variant of a respiratory mask. In this mask, the covering device 2 is embodied as stitched by means of seam segments 2a, 2b, 2c, 2d. The course of the seam segments and the shape of the woven zones located between them are adapted such that the covering device is given a defined shape under the influence of the respiratory gas pressure.

It is also possible to place the covering device on a ribbed structure, or to embody it as an insert element for a hard shell.

Instead of a woven material, nonwoven or filter materials or other kinds of porous materials may be used, such as micro perforated plastic films.

FIG. 3 shows a detail of a covering device made from a woven material.

FIG. 4 shows warp threads 5 and weft threads 6 of the woven portion of FIG. 3. Between the warp and weft threads, interstices are defined through which $CO_2$-laden respiratory gas can escape from the mask interior.

FIG. 5 shows an insert element for a hard mask shell. The insert element includes a porous zone 7, which is made from an air-permeable material. Via this porous zone, $CO_2$-laden respiratory gas can escape from the mask interior.

Figure 8B:
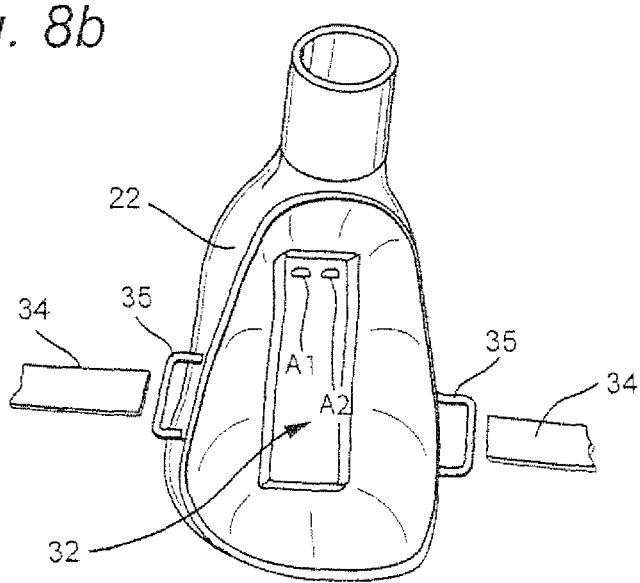

The respiratory masks described can be secured by means of headband arrangements, e.g., headband 34 connecting to headgear connectors 35, as illustrated in FIG. 8b. These headband arrangements can be used to evacuate respiratory gas, because they may have air-permeable zones which communicate with the mask interior via a conduit.

Figure 6:
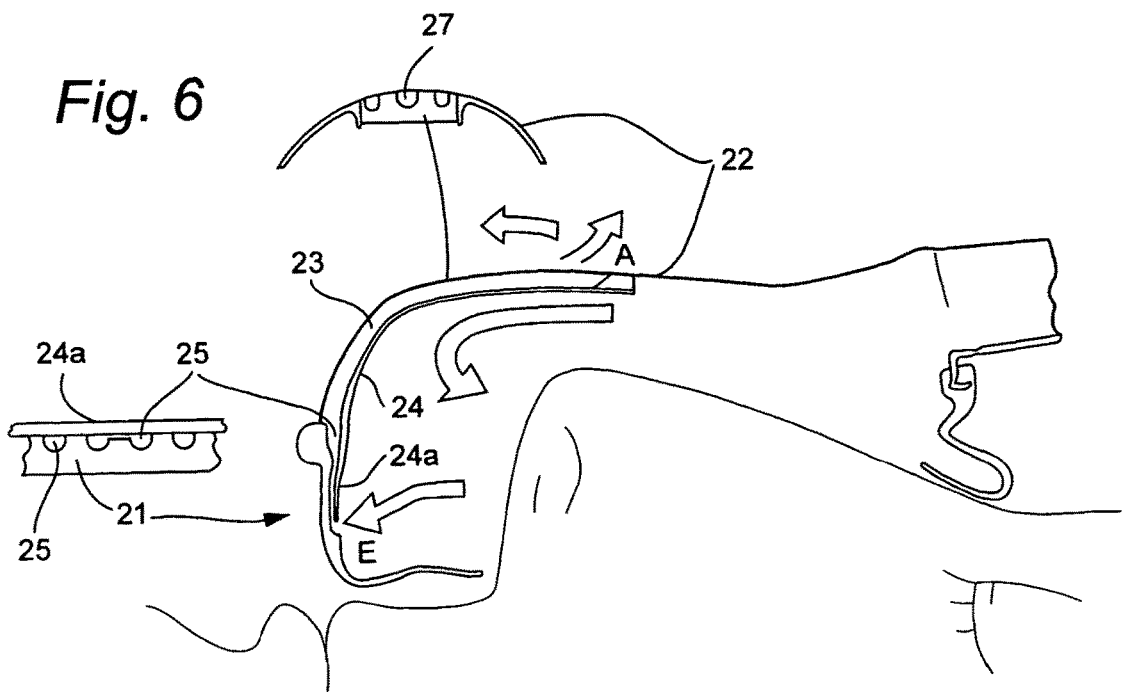
FIG. 6, a sketch for explaining an embodiment of the invention for attaining the second aspect of the object of the invention.

The respiratory mask arrangement shown in FIG. 6 includes a sealing lip device 21, made from an elastomer material, in particular silicone rubber, and an arched member 22. The sealing lip device 21 is embodied such that it encompasses a receiving opening, intended to receive the nasal region of a mask user, and preferably crosses over the bridge of the nose and the upper lip region of the mask user. The sealing lip device 21 thus has a substantially saddle-shaped silhouette.

The arched member is embodied such that it defines an air guide path 23, which extends from a respiratory gas inlet area E to a respiratory gas outlet area A, and extends at least in some portions along a wall that defines the arched member 22.

The air guide path 23 is defined, toward the mask interior region, by an insert element 24. The arched member 22 is also provided with a fixation device, for installing the insert element 24. A covering portion 24a is embodied on the insert element 24 and rests on a fluted conduit structure 25, which is embodied in the inner region of the sealing lip device 21.

Figure 7:
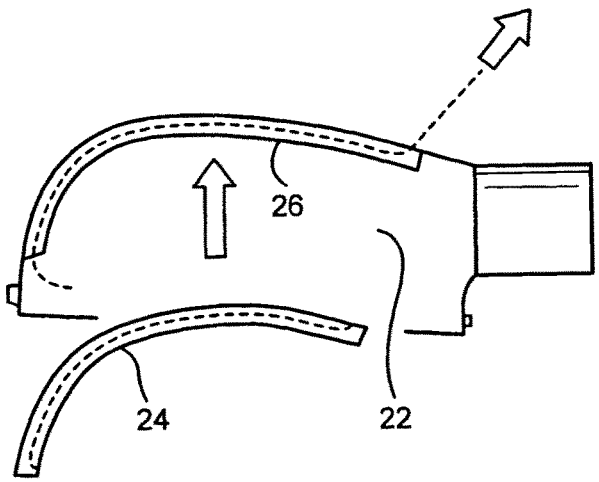
FIG. 7, a sketch for explaining a preferred construction of a hard shell and of an insert element intended to be inserted into it.

As can be seen from FIG. 7, the insert element 24 can be installed in the inner region of the arched member 22. A receiving portion 26 is embodied in the inner region of the arched member 22, for receiving the insert element 24.

Figure 8A:
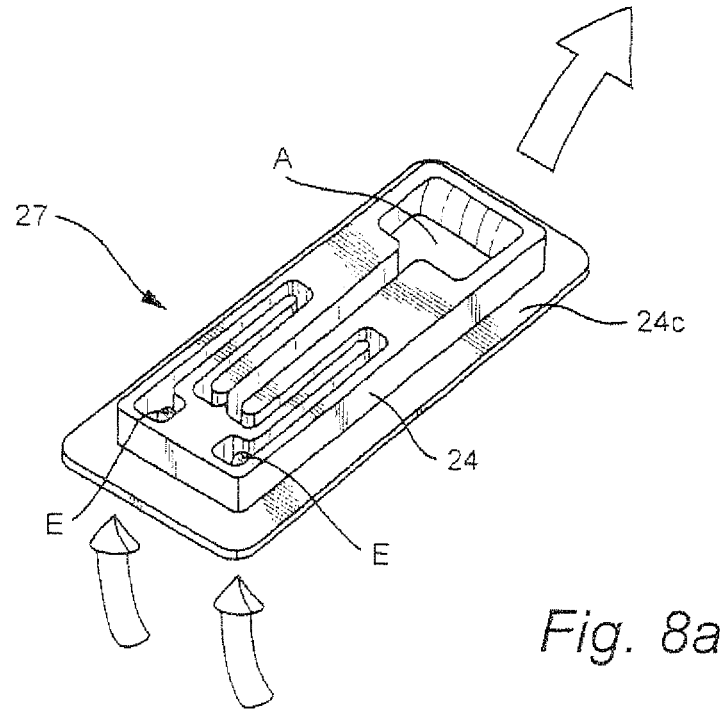
FIG. 8a, a sketch for explaining a preferred embodiment of an insert element of the application structure of the respiratory mask arrangement shown above.

As can be seen from FIG. 8a, conduit structures 27 are embodied in the insert element 24. The conduit structures 27 are adapted such that a defined flow resistance is obtained. The conduit structures 27 extend from an inlet region E to an outlet region A. In the installed state, the conduit portions 27 are covered by the wall of the arched member 22. The insert element 24 is made from an elastomer material. In the insert element 24, labyrinth structures are formed by the conduit portions 27. The insert element 24 can be coupled to the arched member by clamping action. For additional sealing, a sealing lip 24c extending all the way around is embodied on the insert element 24. The insert element 24 shown here can be inserted from the inside into the arched member 22 shown in FIG. 8b.

As can be seen from FIG. 8b, there are outlet openings A1, A2 in the arched member 22, which match the outlet region A of the insert element and make an outflow of the used breathing air possible. In this exemplary embodiment, the arched member 22 itself is made of a thermoplastic material. The receiving region 32 intended for receiving the insert element 24 can be defined by an indentation or by a circumferential wall.

It is also possible to accomplish the fixation of the insert element by means of pegs or other retention means.

The insert element is embodied here by a low rectangular body. It is also possible to design the insert element in some other way, in particular as a cylindrical disk or as a polygonal prism. The insert element can also be designed such that certain throttling effects are obtained as a result of its position on the arched member.

The insert element may also be designed such that as a function of the internal pressure, various flow resistances are obtained, in particular by deformation of the conduit portions 27.

The invention claimed is:

1. A respiratory mask arrangement comprising:
   a sealing portion for resting on and forming a seal with a facial surface of a mask user,
   a covering portion which in cooperation with the sealing portion defines a mask interior,
   a headband arrangement coupled to the covering portion,
   a respiratory gas conduit for delivering respiratory gas to the mask interior defined by the covering portion, the mask interior configured to communicate with the nostril opening of the mask user when the mask is worn, wherein the respiratory gas conduit is connected to the covering portion, the covering portion includes a woven material to which the conduit is directly connected, and the covering portion is configured to be inflated under the influence of the respiratory gas when the mask is worn.

2. The respiratory mask arrangement in accordance with claim 1, wherein the woven material comprises an air-permeable woven material.

3. The respiratory mask arrangement in accordance with claim 1, wherein the covering portion is made from a porous material.

4. The respiratory mask arrangement in accordance with claim 1, wherein the covering portion is a flexible material.

5. The respiratory mask arrangement in accordance with claim 2, wherein an air permeability of the air-permeable woven material and an area of a portion defined thereby are selected to produce outflow of gas from the mask interior.

6. The respiratory mask arrangement in accordance with claim 1, wherein the sealing portion is glued or vulcanized or sprayed onto the covering portion.

7. The respiratory mask arrangement in accordance with claim 1, wherein the covering portion is detachably coupled with the sealing portion.

8. The respiratory mask arrangement in accordance with claim 1, wherein the sealing portion is embodied integrally with the covering portion.

9. The respiratory mask arrangement in accordance with claim 1, wherein the woven material covers substantially an entire front side of the respiratory mask.

10. The respiratory mask arrangement in accordance with claim 1, wherein the woven material extends over substantially an entire area of the covering portion.

11. A respiratory mask, comprising:
    a covering portion of a woven material, the covering portion covering substantially an entire front side of the mask,
      a respiratory gas conduit connected to the woven material of the covering portion for delivering respiratory gas to the respiratory mask,
      a receiving portion formed on a back side of the mask, the receiving portion for receiving a nasal region of a user,
    a seal portion for forming a seal with the nasal region of the user,
      a first headband connector disposed on a first lateral side of the covering portion and a second headband connector disposed on a second lateral side of the covering portion, and
      a headband arrangement connected to the first headband connector and the second headband connector for securing the respiratory mask to the user, wherein the covering portion is configured to be inflated under the influence of the respiratory gas when the mask is worn.

12. The respiratory mask of claim 11, wherein the covering portion is flexible.

13. The respiratory mask of claim 11, wherein the covering portion is an air-permeable woven.

14. The respiratory mask of claim 11, wherein the covering portion is porous.

15. The respiratory mask of claim 11, wherein the receiving opening is shaped to form a seal with an upper lip region and a bridge of the nose region of the user.

16. The respiratory mask of claim 11, wherein the headband arrangement is connected to covering portion at side portions of the covering portion.

17. A respiratory mask for delivering breathable gas to a patient at a level that is above ambient pressure, the mask comprising:
    a mask body including a front portion and a rear portion opposite the front portion, the front portion and the rear portion cooperating to define a mask interior to communicate with a source of pressurized gas,
    the rear portion including a seal portion to cross over the patient's nasal bridge region and seal around the patient's nose or the patient's nose and mouth when the mask is worn, and a receiving opening surrounded by the seal portion to receive the patient's nose or the patient's nose and mouth within the mask interior when the mask is worn,
    the front portion including a gas outflow area to provide a diffuse outflow of gas from the mask interior to atmosphere,
    a pair of headgear connectors, one of said pair of connectors extending laterally away from each side of the mask body,
    a headband arrangement coupled to each said headgear connector to support the mask body on the patient's head when the mask is worn,
    the front portion comprising a flexible portion of material which is configured to be inflated under the influence of the pressurized gas when the mask is worn, the flexible portion extending across the mask body from one side of the mask body to the other,
    the flexible portion of material includes at least one stitched seam segment, the at least one stitched seam segment and a shape of the flexible portion of material being configured and arranged to provide a defined shape upon supply of the pressurized gas to the mask interior, and
    a connection stub coupled to the flexible portion of material and adapted to be coupled to a respiratory gas hose.

18. The respiratory mask of claim 17, wherein the flexible portion of material comprises a plastic film having perforations to act as the gas outflow area.

19. The respiratory mask of claim 17, wherein the flexible portion of material comprises a woven material, a non-woven material, a filter material, or a porous material.

20. The respiratory mask of claim 17, wherein the flexible portion of material includes warp threads and weft threads, with interstices therebetween.

21. The respiratory mask of claim 17, wherein the flexible portion of material comprises a layer of woven material.

22. The respiratory mask of claim 21, wherein the woven material is air-permeable.

23. The respiratory mask of claim 17, wherein the seal portion includes an elastomer portion at least in an upper lip region of the seal portion.

24. The respiratory mask of claim 17, wherein the seal portion includes an upper lip region to seal against an upper lip region of the patient when the mask is worn.

25. The respiratory mask of claim 17, wherein the at least one stitched seam segment comprises a plurality of stitched seam segments.

26. The respiratory mask of claim 25, wherein the plurality of stitched seam segments comprise a plurality of vertical stitched seam segments.

27. The respiratory mask of claim 25, wherein a plurality of woven material zones are defined between the plurality of stitched seam segments.

28. The respiratory mask of claim 27, wherein the course of the stitched seam segments and a shape of the woven material zones are adapted to provide the defined shape upon supply of the pressurized gas to the mask interior.

29. A respiratory mask for delivering breathable gas to a patient at a level that is above ambient pressure, the mask comprising:
   a mask body including a front portion and a rear portion opposite the front portion, the front portion and the rear portion cooperating to define a mask interior to communicate with a source of pressurized gas,
   the rear portion including a nasal bridge region and 1) a nose region or 2) a nose region and a mouth region, the rear portion including a receiving opening to receive the patient's nose or the patient's nose and mouth within the mask interior when the mask is worn,
   the front portion including a gas outflow area to provide a diffuse outflow of gas from the mask interior to atmosphere,
   a pair of headgear connectors, one of said pair of connectors extending laterally away from each side of the mask body,
   a headband arrangement coupled to each said headgear connector to support the mask body on the patient's head when the mask is worn,
   the front portion consisting essentially of a flexible portion of material which is configured to be inflated under the influence of the pressurized gas when the mask is worn, and
   a connection stub coupled to the flexible portion of material and adapted to be coupled to a respiratory gas hose.

30. The respiratory mask of claim 29, wherein the flexible portion of material is a woven material, a non-woven material, a filter material, or a porous material.

31. The respiratory mask of claim 30, wherein the flexible portion comprises a woven material that is air-permeable.

32. The respiratory mask of claim 29, wherein the flexible portion of material comprises a plastic film having perforations to act as the gas outflow area.

33. The respiratory mask of claim 29, wherein the flexible portion of material includes warp threads and weft threads, with interstices therebetween.

34. The respiratory mask of claim 29, wherein the rear portion includes an elastomer portion at least in an upper lip region thereof.

35. The respiratory mask of claim 29, wherein the rear portion includes an upper lip region to seal against an upper lip region of the patient when the mask is worn.

36. The respiratory mask of claim 29, wherein the flexible portion includes a woven material layer and an impermeable material layer applied to the woven material layer.

37. A respiratory mask for delivering breathable gas to a patient at a level that is above ambient pressure, the mask comprising:
   a mask body including a front portion and a rear portion opposite the front portion, the front portion and the rear portion cooperating to define a mask interior to communicate with a source of pressurized gas,
   the rear portion including a nasal bridge region and a lip region, the rear portion including a receiving opening to receive the patient's nose or the patient's nose and mouth within the mask interior when the mask is worn,
   the front portion including a top portion opposite from the nasal bridge region and a bottom portion opposite from the lip region, and the front portion including a gas outflow area to provide a diffuse outflow of gas from the mask interior to atmosphere,
   a pair of headgear connectors, one of said pair of connectors extending laterally away from each side of the mask body,
   a headband arrangement coupled to each said headgear connector to support the mask body on the patient's head when the mask is worn,
   the front portion consisting essentially of a flexible portion of woven air-permeable material which is configured to be inflated under the influence of the pressurized gas when the mask is worn, the flexible portion of material extending on the front portion over substantially an entire area between the pair of headgear connectors and between the top portion and the bottom portion, and
   a connection stub coupled to the flexible portion of material and adapted to be coupled to a respiratory gas hose.

38. The respiratory mask of claim 37, wherein the rear portion includes an elastomer portion at least in the lip region thereof.

39. The respiratory mask of claim 37, wherein the flexible portion has perforations to act as the gas outflow area.

* * * * *